United States Patent [19]

Kawakita et al.

[11] Patent Number: 4,720,493
[45] Date of Patent: Jan. 19, 1988

[54] THIENYLTHIAZOLE COMPOUNDS

[75] Inventors: Takeshi Kawakita, Nakatsu; Mitsuharu Sano; Mitsuyoshi Yasumoto, both of Fukuoka; Kunio Ohsuga; Kei-ichiro Haga, both of Nakatsu, all of Japan

[73] Assignee: Yoshitomi Pharmaceutical Industries, Ltd., Osaka, Japan

[21] Appl. No.: 799,989

[22] Filed: Nov. 20, 1985

[30] Foreign Application Priority Data

Nov. 22, 1984 [WO] PCT Int'l Appl. .............. 00562

[51] Int. Cl.⁴ .................. C07D 417/04; A61K 31/425
[52] U.S. Cl. ..................................... 514/230; 514/252; 514/326; 514/370; 514/371; 544/133; 544/333; 544/367; 546/209; 546/280; 548/193; 548/194; 548/195
[58] Field of Search .............. 548/190, 193, 194, 195; 546/280, 209; 544/133, 367, 333; 514/230, 252, 326, 370, 371

[56] References Cited

U.S. PATENT DOCUMENTS

| | | | |
|---|---|---|---|
| 4,307,106 | 12/1981 | Lombardino | 548/190 |
| 4,374,843 | 2/1983 | La Mattina | 514/256 |
| 4,435,396 | 3/1984 | La Mattina | 514/256 |
| 4,560,690 | 12/1985 | Reter | 514/256 |

FOREIGN PATENT DOCUMENTS

| | | |
|---|---|---|
| 52564 | 5/1982 | European Pat. Off. |
| 100018 | 2/1984 | European Pat. Off. |
| 2022085 | 12/1979 | United Kingdom |

OTHER PUBLICATIONS

Chemical Abstracts, 100:122768k, 1984.
Derwent CPI, 33756 K/14.
Derwent CPI, 85-029014/05.

Primary Examiner—Robert Gerstl
Attorney, Agent, or Firm—Wenderoth, Lind & Ponack

[57] ABSTRACT

Thienylthiazole compounds of the formula:

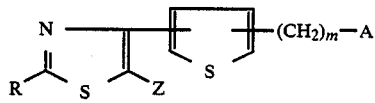

and pharmaceutically acceptable acid addition salts thereof, wherein:

R is amino, guanidino, alkylamino, alkenylamino, unsubstituted or optionally substituted phenylamino or acylamino;

A is amino, alkylamino, cyclic amino, alkanoylamino, a group of the formula:

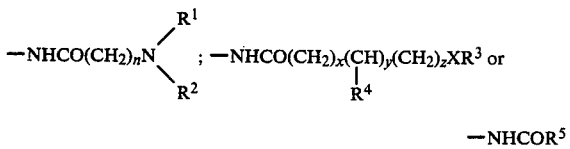

$$-NHCOR^5$$

wherein each symbol is as defined in claim 1;
Z is hydrogen or halogen; and
m is 0 or 1 to 4, are useful in the treatment of peptic ulcer, acute or chronic gastritis, acute damage of gastric mucous membrane, dimentia and anxiety.

4 Claims, No Drawings

THIENYLTHIAZOLE COMPOUNDS

BACKGROUND OF THE INVENTION

1. Field of the Invention

The present invention relates to novel and therapeutically valuable thienylthiazole compounds, methods of preparing said compounds and a pharmaceutical composition comprising at least one of said compounds.

2. Description of the Prior Art

Peptic ulcer is caused by various factors, especially by loss of balance between aggressive factors such as gastric juice and defensive factors such as resistance of gastric mucosa.

Histamine $H_2$ receptor blockers represented by cimetidine exhibit inhibitory activity on such aggressive factors, namely inhibit the gastric secretion by specifically binding with the histamine receptor on the cellular membrane on the gastric wall.

Recently, famotidine, 1-amino-3-(2-guanidino-4-thiazolylmethylthio)-propylidene)sulfamide, has been developed as a new histamine $H_2$ receptor blocker.

On the other hand, prostaglandins are known to potentiate the defensive factors and be useful as cytoprotective antiulcer agents, since they suppress gastric acid secretion and, in lower doses, have specific protective effects on gastric mucosa against many stimuli.

Under these circumstances, compounds having both aggressive factor-inhibitory activity and defensive factor-potentiating activity have been desired.

U.S. Pat. No. 4307106 and the corresponding Japanese Patent Application (Kokai) No. 160369/79 disclose a series of 2-aralkylaminothiazoles having anti-inflammatory and immune regulant activity.

Japanese Patent Application (Kokai) No. 35186/83 discloses dicarboxyaminothiazole derivatives having immunocontrolling activity.

European Patent Application No. 100018 discloses the production of 2-N,N-di-substituted-aminothiazoles which are useful as intermediates for dyestuffs.

SUMMARY OF THE INVENTION

As a result of various investigations, the present inventors have found that novel thienylthiazole compounds and pharmaceutically acceptable acid addition salts thereof exhibit potent antiulcer, antihypoxia, antiamnesia and anti-anxiety activities.

DETAILED DESCRIPTION OF THE INVENTION

The thienylthiazole compounds of the present invention are represented by the following formula:

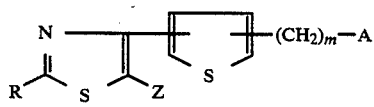  (I)

In the above formula, each symbol is defined as follows:

R is amino, guanidino, mono- or di-alkylamino, alkenylamino, mono- or di-phenylamino which may be optionally substituted by at least one substituent selected from the group consisting of halogen, alkyl, trifluoromethyl, alkoxy, nitro and amino on the phenyl nucleus, or acylamino;

A is amino, mono- or di-alkylamino, cyclic amino, alkanoylamino, a group of the formula:

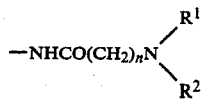

(wherein each of $R^1$ and $R^2$ is hydrogen or alkyl, or $R^1$ and $R^2$ together with the adjacent nitrogen atom form a heterocycle, and n is O or an integer of 1 to 3); a group of the formula:

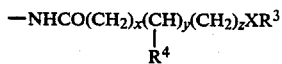

(wherein $R^3$ is hydrogen, alkyl, alkanoyl, mono- or di-alkylaminoalkyl, or aryl, aralkyl or heteroaryl which may be optionally substituted, on the aromatic(hetero) ring, by at least one substituent selected from the group consisting of halogen, amino, nitro, alkyl, alkoxy, mono- or di-alkylamino, mono-or di-alkylaminoalkyl and cyclic aminoalkyl; $R^4$ is hydrogen or alkyl; X is oxygen or sulfur, and each of x, y and z is O or an integer of 1 to 3 provided that the sum of x, y and z being 3 or less); or a group of the formula:

(wherein $R^5$ is aryl, aralkyl or heteroaryl which may be optionally substituted, on the aromatic(hetero) ring, by at least one substituent selected from the group consisting of halogen, amino, nitro, alkyl, alkoxy, mono- or di-alkylamino, mono-or di-alkylaminoalkyl and cyclic aminoalkyl);

Z is hydrogen, halogen; and m is O or an integer of 1 to 4.

In the present specification, each substituent is defined as follows:

halogen means chlorine, bromine, fluorine or iodine;

alkyl means $C_{1-10}$ alkyl such as methyl, ethyl, propyl, isopropyl, butyl, isobutyl, tert-butyl, pentyl, isopentyl, neopentyl, hexyl, heptyl, octyl, 2-ethylhexyl, nonyl or decyl;

alkoxy means $C_{1-10}$ alkoxy such as methoxy, ethoxy, propoxy, isopropoxy, butoxy, isobutoxy, tert-butoxy, pentyloxy, isopentyloxy, neopentyloxy, hexyloxy, heptyloxy, octyloxy, 2-ethylhexyloxy, nonyloxy or decyloxy;

alkanoyl means $C_{2-12}$ alkanoyl such as acetyl, propionyl, butyryl, pivaloyl, valeryl, hexanoyl, decanoyl or lauroyl;

mono- or di-alkylamino means mono- or di-$C_{1-6}$alkylamino such as methylamino, ethylamino, propylamino, isopropylamino, butylamino, tert-butylamino, pentylamino, hexylamino, dimethylamino, diethylamino, dipropylamino, diisopropylamino, dibutylamino, ditertbutylamino, dipentylamino or dihexylamino;

alkenylamino means $C_{2-5}$ alkenylamino such as vinylamino, allylamino, 1-propenylamino, isopropenylamino, 2-butenylamino or 2-pentenylamino;

mono- or di-phenylamino which may be substituted by at least one substituent selected from the group consisting of halogen, alkyl, trifluoromethyl, alkoxy, nitro and amino on the phenyl nucleus includes phenylamino, diphenylamino, chlorophenylamino, bromophenylamino, fluorophenylamino, methylphenylamino, ethylphenylamino, propylphenylamino, isopropylphenylamino, butylphenylamino, tert-butylphenylamino, trifluoromethylphenylamino, methoxyphenylamino, ethoxyphenylamino, propoxyphenylamino, butoxyphenylamino, nitrophenylamino, aminophenylamino, dichlorophenylamino, dimethylphenylamino, trimethoxyphenylamino, bis(chlorophenyl)amino, bis (fluorophenyl)amino, bis(methylphenyl)amino, bis(ethylphenyl) amino, bis(propylphenyl)amino, bis(butylphenyl)amino, bis (methoxyphenyl)amino, bis(ethoxyphenyl)amino, bis(propoxyphenyl) amino, bis(butoxyphenyl)amino, bis(nitrophenyl)amino, bis(aminophenyl)amino, N-phenyl-N-chlorophenylamino or N-fluorophenyl-N-methylphenylamino;

acylamino means $C_{2-12}$ alkanoylamino such as acetylamino, propionylamino, butyrylamino, pivaloylamino, valerylamino, hexanoylamino or lauroylamino, and benzoylamino which may substituted by at least one substituent selected from the group consisting of halogen, alkyl, trifluoromethyl, alkoxy, nitro and amino on the phenyl nucleus such as benzoylamino, chlorobenzoylamino, bromobenzoylamino, fluorobenzoylamino, methylbenzoylamino, ethylbenzoylamino, propylbenzoylamino, butylbenzoylamino, trifluoromethylbenzoylamino, methoxybenzoylamino, ethoxybenzoylamino, propoxybenzoylamino, butoxybenzoylamino, nitrobenzoylamino, aminobenzoylamino, dichlorobenzoylamino or trimethoxybenzoylamino;

cyclic amino means saturated 5 to 7 membered cyclic ring which may further contain at least one heteroatom selected from the group consisting of oxygen atom and optionally substituted nitrogen atom such as 1-pyrrolidinyl, piperidino, 4-methyl-piperazinyl, 4-(2-hydroxyethyl)-1-piperazinyl, 4-phenyl-1-piperazinyl which may be optionally substituted, on the phenyl nucleus, by at least one substituent selected from the group consisting of halogen, alkyl, trifluoromethyl and alkoxy such as 4-phenyl-1-piperazinyl, 4-chlorophenyl-1piperazinyl, 4-bromophenyl-1-piperazinyl, 4-fluorophenyl-1-piperazinyl, 4-methylphenyl-1-piperazinyl, 4-methylphenyl-1-piperazinyl, 4-ethylphenyl-1-piperazinyl, 4-propylphenyl-1-piperazinyl, 4-butylphenyl-1-piperazinyl, 4-trifluoromethylphenyl-1-piperazinyl, 4-methoxyphenyl-1-piperazinyl, 4-ethoxyphenyl-1-piperazinyl, 4-propoxyphenyl-1-piperazinyl, 4-butoxyphenyl-1-piperazinyl, 4-dichlorophenyl-1-piperazinyl or 4-trimethoxyphenyl-1-piperazinyl, or 4-pyrimidinyl-1-piperazinyl, 1-homopiperazinyl or morpholino;

alkanoylamino means $C_{2-12}$ alkanoylamino such as acetylamino, propionylamino, butyrylamino, pivaloylamino, valerylamino, hexanoylamino, decanoylamino or lauroylamino;

heterocycle which can be formed together with the adjacent nitrogen atom means saturated or unsaturated 5 to 7 membered heterocycle which may further contain at least one heteroatom selected from the group consisting of oxygen atom and optionally substituted nitrogen atom such as 1-pyrrolidinyl, piperidino, 1-piperazinyl, 4-methyl-1-piperazinyl, 4-(2-hydroxyethyl)-1-piperazinyl, 4-phenyl-1-piperazinyl, which may be substituted, on the phenyl nucleus, by at least one substituent selected from the group consisting of halogen alkyl and trifluoromethyl such as 4-phenyl-1-piperazinyl, 4-chlorophenyl-1-piperazinyl, 4-fluorophenyl-1-piperazinyl, 4-methylphenyl-1-piperazinyl, 4-ethylphenyl-1-piperazinyl, 4-propylphenyl-1-piperazinyl, 4-butylphenyl-1-piperazinyl or trifluoromethylphenyl-1-piperazinyl, or 1-homopiperazinyl, morpholino or imidazoyl;

mono- or di-alkylaminoalkyl means mono- or di-$C_{1-5}$ alkylamino-$C_{1-4}$ alkyl such as methylaminomethyl, ethylaminomethyl, propylaminomethyl, isopropylaminomethyl, butylaminomethyl, tert-butylaminomethyl, pentylaminomethyl, 2-methylaminoethyl, 2-ethylaminoethyl, 2-propylaminoethyl, 2-butylaminoethyl, 3-methylaminopropyl, 3-ethylaminopropyl, 3-propylaminopropyl, 3-butylaminopropyl, 4-methylaminobutyl, 4-ethylaminobutyl, 4-propylaminobutyl, 4-butylaminobutyl, dimethylaminomethyl, diethylaminomethyl, dipropylaminomethyl, diisopropylaminomethyl, dibutylaminomethyl, di-tert-butylaminomethyl, 2-dimethylaminoethyl, 2-diethylaminoethyl, 2-dipropylaminoethyl, 2-dibutylaminoethyl, 3-dimethylaminopropyl, 3-diethylaminopropyl, 3-dipropylaminopropyl, 3-dibutylaminopropyl, 4-dimethylaminobutyl, 4-diethylaminobutyl, 4-dipropylaminobutyl or dibutylaminobutyl;

cyclic aminoalkyl means saturated 5 to 7 membered cyclic amino-$C_{1-4}$ alkyl and may further contain, in the cyclic amino moiety, at least one heteroatom selected from the group consisting of oxygen atom and optionally substituted nitrogen atom, and includes, for example, 1-pyrrolidinylmethyl, 2-(1-pyrrolidinyl)butyl, piperidinomethyl, 2-piperidinoethyl, 3-piperidinopropyl, 4-piperidinobutyl, 4-methyl-1-piperazinyl methyl, 2-(4-methyl-1-piperazinyl)ethyl, morpholinomethyl, 2-morpholinoethyl, 3-morpholinopropyl or 4-morpholinobutyl;

in the aryl, aralkyl or heteroaryl which may be optionally substituted, on the aromatic(hetero) ring, by at least one substituent selected from the group consisting of halogen, amino, nitro, alkyl, alkoxy, mono- or di-alkylamino, mono-or di-alkylaminoalkyl and cyclic aminoalkyl, the substituents, i.e. halogen, alkyl, alkoxy, mono- or di-alkylamino, mono-or di-alkylaminoalkyl and cyclic aminoalkyl, are as defined above and the aryl moiety includes phenyl or naphthyl, the aralkyl moiety includes benzyl, 2-phenylethyl or 3-phenylpropyl, and the heteroaryl moiety includes 2-pyridyl, 3-pyridyl, 4-pyridyl, 2-furyl, 3-furyl, 2-thienyl or 3-thienyl; Preferable compounds of the present invention are the compounds of the formula (I) wherein R is amino or phenylamino; A is amino, mono- or di-alkylamino, cyclic amino, alkanoylamino or the group of formula:

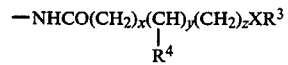

wherein each symbol is as defined above; Z is hydrogen; and m is 0 or an integer of 1 to 4.

The "2-aminothiazole" moiety in the compounds of the present invention can also be expressed as its tautomeric form, "2-iminothiazoline". The present invention embraces these tautomers because they are in equilibrium. The compounds of the present invention are described as 2-aminothiazole throughout the specification.

The compounds of formula (I) can be prepared according to one of the following methods:

(1) A compound of the formula:

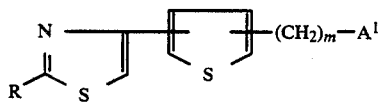 (I-a)

wherein $A^1$ is mono- or di-alkylamino, cyclic amino or alkanoylamino in the definition of the symbol A; and R and m are as defined above, can be prepared by reacting a compound of the formula:

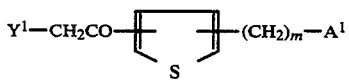 (II)

wherein $Y^1$ is halogen and other symbols are as defined above, with a compound of the formula:

$$RCSNH_2 \quad (III)$$

wherein R is as defined above.

The reaction is usually carried out at room temperature or under heating or refluxing for 1–24 hours in an inert solvent such as methanol, ethanol, acetone, chloroform or dimethylformamide.

The starting compound of formula (II) can be prepared by reacting a compound of the formula:

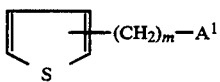 (IV)

wherein each symbol is as defined above, with a compound of the formula:

$$CH_3CO-Y^2 \quad (V)$$

wherein $Y^2$ is chlorine or bromine, and reacting thus obtained compound of the formula:

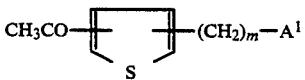 (VI)

wherein each symbol is as defined above, with a halogenating agent.

The reaction of the compound of formula (IV) with the compound of the formula (V) is usually carried out at, preferably, 0° C. to room temperature for 15 minutes to 4 hours in the presence of a catalyst such as Lewis acid (e.g. anhydrous aluminum chloride, ferric chloride or stannic chloride) in a solvent such as dichloromethane, dichloroethane or nitrobenzene.

The reaction of the compound of formula (VI) with the halogenating agent is usually carried out at, preferably, 0°–40° C. for 30 minutes to 5 hours in an inert solvent such as chloroform, dichloromethane, methylene chloride, carbon tetrachloride or acetic acid.

The halogenating agent includes, for example, bromine, chlorine, N-bromosuccinimide or N-chlorosuccinimide.

The compound of formula (II) can also be prepared by reacting the compound of formula (IV) with a compound of the formula:

$$Y^1CH_2COY^3 \quad (VII)$$

wherein $Y^3$ is chlorine or bromine and $Y^1$ is as defined above.

The reaction is usually carried out at, preferably, room temperature to refluxing temperature for 15 minutes to 4 hours in the presence of a catalyst such as Lewis acid (e.g. anhydrous aluminum chloride, ferric chloride or stannic chloride) in a solvent such as dichloromethane, dichloroethane or nitrobenzene.

(2) A compound of the formula:

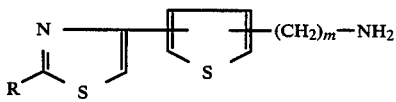 (I-b)

wherein each symbol is as defined above, can be prepared by subjecting a compound of the formula:

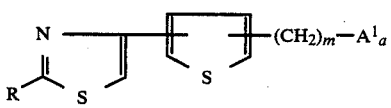 (I-a')

wherein $A_a^1$ is alkanoylamino in the definition of the symbol $A^1$ and other symbols are as defined above, to hydrolysis.

The reaction is usually carried out at room temperature or under heating for 1–24 hours in the presence of an acid such as sulfuric acid, hydrochloric acid, hydrobromic acid or phosphoric acid or a base such as sodium hydroxide or potassium hydroxide in water or an aqueous solvent such as aqueous methanol, aqueous ethanol, aqueous dioxane or aqueous tetrahydrofuran.

(3) A compound of the formula:

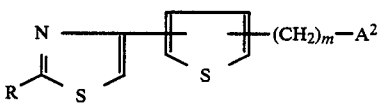 (I-c)

wherein $A^2$ is, in the definition of the symbol A, the group of formula:

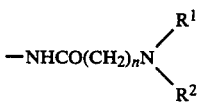

wherein each symbol is as defined above, the group of the formula:

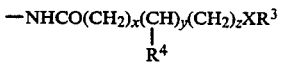

wherein each symbol is as defined above, or the group of the formula:

$$-NHCOR^5$$

wherein $R^5$ is as defined above, and other symbols are as defined above, can be prepared by reacting the compound of formula (I-b) with a compound of the formula:

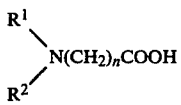 (VIII)

wherein each symbol is as defined above, or a compound of the formula:

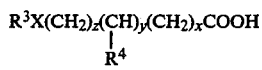 (IX)

wherein each symbol is as defined above, or a compound of the formula:

 (X)

wherein $R^5$ is as defined above, or functional derivatives thereof.

In case that the compounds of formulas (VIII), (IX) and (X) are free carboxylic acids, the reaction is usually carried out in the presence of a condensing agent such as dicyclohexylcarbodiimide, titanium tetrachloride, phosphorus trichloride, phosphorus oxychloride or diphenylphosphoryl azide in an inert solvent such as water, methanol, ethanol, isopropanol, ethyl acetate, benzene, toluene, acetone, tetrahydrofuran, dioxane, dimethylformamide or dimethyl sulfoxide or a mixture thereof under cooling, at room temperature or under heating.

The functional derivatives of the compounds of formulas (VIII), (IX) and (X) include, for example, an acid halide (e.g. an acid chloride or an acid bromide), an acid anhydride, a mixed acid anhydride (e.g. a mixed acid anhydride with a lower alkanoic acid or a mixed acid anhydride with an alkylphosphoric acid), a lower alkyl ester or an active ester (e.g. p-nitrophenyl ester, p-nitrobenzyl ester or p-chlorophenyl ester).

The reaction with the acid halide is usually carried out by stirring at 0°-80° C., preferably at 10°-35° C. for 10 minutes to 24 hours, preferably 10-60 minutes in the presence of a deacidifying agent such as triethylamine, pyridine or 4-dimethylaminopyridine in a non-aqueous solvent such as chloroform, methylene chloride or benzene.

The reaction with the mixed acid anhydride is usually carried out by stirring at 0°-45° C. for 1-10 hours, preferably in a solvent such as chloroform or tetrahydrofuran.

The reaction with the ester is usually carried out by refluxing for 1-48 hours, preferably in an alcohol solvent such as methanol, ethanol or butanol.

(4) A compound of the formula (I) wherein Z is halogen can be prepared by reacting a compound of the formula:

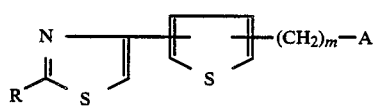 (I-d)

wherein each symbol is as defined above, with a halogenating agent.

The halogenating agent includes, for example, chlorine, bromine, N-chlorosuccinimide or N-bromosuccinimide. The reaction is usually carried out at 0°-80° C. for 1 to 24 hours in an inert solvent such as chloroform or acetic acid.

(5) A compound of the formula:

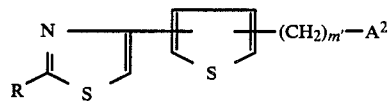 (I-e)

wherein $A^2$ is mono- or di-alkylamino or cyclic amino in the definition of the symbol A, m' is an integer of 2 to 4 and R is as defined above, can be prepared by reacting a compound of the formula:

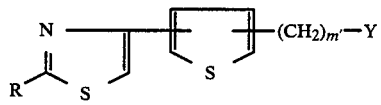 (XI)

wherein Y is halogen and other symbols are as defined above, with a compound of the formula:

 (XII)

wherein $A^2$ is as defined above.

The reaction is usually carried out at a temperature from room temperature to 140° C., preferably at 50°-110° C. for 1-48 hours, preferably for 3-18 hours in the presence of a base such as potassium carbonate, sodium carbonate or triethylamine in an inert solvent such as methanol, ethanol, benzene, toluene, xylene, dichloroethane, chloroform, acetone, methyl ethyl ketone or dimethylformamide. It is advantageous to use an iodide compound such as potassium iodide or sodium iodide in case that the compound of formula (XI) wherein Y is other than iodine is employed as a starting compound.

The starting compound of formula (XI) can be prepared by reacting a compound of the formula:

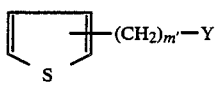 (XIII)

wherein each symbol is as defined above, with a compound of the formula:

 (XIV)

wherein $Y^4$ is halogen; reacting thus obtained compound of the formula:

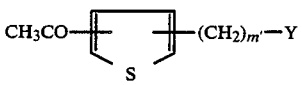 (XV)

wherein each symbol is as defined above, with a halogenating agent; and reacting thus obtained compound of the formula:

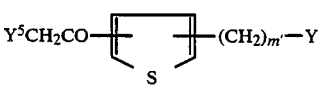 (XVI)

wherein $Y^5$ is halogen and other symbols are as defined above, with the compound of formula (III).

The compound of formula (XV) can be prepared by subjecting to Friedel-Crafts reaction the compound of formula (XIII) with the compound of formula (XIV) in the presence of a Lewis acid such as aluminum chloride or stannic chloride.

The reaction is usually carried out at 0°–80° C., preferably at 0°–20° C. for 1–8 hours in an inert solvent such as dichloromethane, dichloroethane, chloroform or benzene.

The halogenating agent employed in the preparation of the compound of formula (XVI) includes, for example, chlorine or bromine. This reaction is usually carried out at 0°–80° C. for 1 to 24 hours in an inert solvent such as chloroform or acetic acid.

The reaction of the compound of formula (XVI) with the compound of formula (III) to obtain the compound of formula (XI) is usually carried out at room temperature or under heating or refluxing for 1–24 hours in an inert solvent such as methanol, ethanol, acetone, chloroform or dimethylformamide.

(6) A compound of formula (I) wherein R is mono- or dialkylamino or alkanoylamino can be prepared by reacting a compound of formula (I) wherein R is amino with an alkyl halide, or alkanoic acid or a functional derivative thereof.

The alkyl halide includes, for example, an alkyl bromide or an alkyl chloride. The reaction is usually carried out by adding 1 mole or 2 mole equivalents of the alkyl halide at room temperature or under refluxing for 1–24 hours in the presence of a deacidifying agent such as sodium carbonate or potassium carbonate in a solvent such as methanol, ethanol or dimethylformamide.

The reaction with an alkanoic acid or a functional derivative thereof (e.g. an acid halide, a mixed acid anhydride or ester) is carried out under the same condition as the above method (3).

(7) Further, a compound of formula (I) wherein R is guanidino can be prepared by converting a thioureide compound according to the method described in Organic Synthesis, vol. 3, p. 735, 1955, reacting the thioureide compound with, for example, methyl iodide in a solvent such as methanol or ethanol, and reacting thus obtained 2-methylthioisoureide compound with an aqueous ammonia at room temperature or under heating for 1–10 hours.

The compounds of formula (I) having an asymmetric carbon atom can be prepared as racemates. The racemates can be resolved by a conventional method such as use of optically active acid or fractional crystallization. The optically active compounds of formula (I) can also be prepared by using an optically active starting compound.

The compounds of formula (I) thus obtained can be converted into pharmaceutically acceptable acid addition salts thereof in a conventional manner by treating with an inorganic acid such as hydrochloric acid, hydrobromic acid, hydriodic acid, sulfuric acid, nitric acid or phosphoric acid or an organic acid such as maleic acid, fumaric acid, oxalic acid citric acid, succinic acid, tartaric acid, methanesulfonic acid, butyric acid or pamoic acid.

The following pharmacological experiments illustrate the potent effects of the compounds of the present invention.

1. Effect on gastric secretion

The experiment was performed according to the method of Shay et al described in Gastroenterology, vol 5, p. 43, 1945.

Groups of ten female Wistar rats, weighing 130.200 g, were deprived of food and the abdomen of each rat was incised and the pylorus ligated under ether anesthesia. Immediately after pylorus ligation, 10 mg/kg of test compounds were subcutaneously administered. After 4 hours, the gastric contents were collected and centrifuged. The supernatant was regarded as volume of gastric secretion. The acidity of gastric juice was determined by titrating the gastric juice with 0.1N sodium hydroxide to pH 7.0 with an automatic titrator (Kyoto Denshi Kogyo K.K., AT-107).

The percent inhibitions (%) of the compounds of the present invention on volume of gastric juice secretion and acidity of gastric juice were calculated and the results are summarized in Table 1.

TABLE 1

| Test Compound | Percent inhibition (%) | |
| --- | --- | --- |
| | Volume of gastric juice secretion | Acidity of gastric juice |
| Compound of Example 4 | 65 | 38 |
| Compound of Example 5 | 66 | 22 |
| Compound of Example 7 | 80 | 31 |
| Compound of Example 14 | 53 | 39 |
| Compound of Example 50 | 64 | 37 |
| Compound of Example 65 | 61 | 39 |

2. Effect on injury of gastric mucous membrane

Male Wistar rats, weighing 170–250 g, were deprived of food for 48 hours and water for 24 hours and then test compounds were intraperitoneally administered. Thirty minutes after administration of test compounds, 5 ml/kg of ethanol was orally administered. One hour later the stomach of each rat was excised and inflated with 8 ml of a 3% formalin solution. The stomach was incised along the greater curvature and the area ($mm^2$) of gastric injury were measured and summed. The square root of the sum was used as an ulcer index. The percent inhibitions (%) against the control group were calculated and the results are summarized in Table 2.

TABLE 2

| Test Compound | Dose (mg/kg) | Percent inhibition (%) |
| --- | --- | --- |
| Compound of Example 6 | 10 | 59 |
| Compound of Example 7 | 3 | 51 |
| | 10 | 63 |
| Compound of Example 11 | 1 | 73 |
| Compound of Example 14 | 3 | 35 |

3. Effect on hypoxia

According to the method of Nakanishi et al described in Life Science, vol. 13, p. 467, 1973, 30 mg/kg of test compounds were orally administered to groups of six female dd-strain mice and 30 minutes later the survival time, i.e. time required until respiratory failure, was measured under the hypoxia condition of 200 mmHg. The extention of the survival time against the control group was expressed as a percentage and the results are summarized in Table 3.

TABLE 3

| Test Compound | Extention of the survival time |
| --- | --- |
| Compound of Example 1 | 280 |
| Compound of Example 5 | 367 |
| Compound of Example 6 | 278 |

TABLE 3-continued

| Test Compound | Extention of the survival time |
|---|---|
| Compound of Example 14 | 204 |
| Compound of Example 65 | 158 |

4. Antianxiety effect

Test compounds were orally administered to groups of seven male ddY-mice and an hour later 0.6 mg/kg of bicuculline was intraveneously administered. Each mouse was observed for occurrence of tonic seizures for 30 minutes immediately after bicuculline administration. The $ED_{50}$ (mg/kg) was calculated by the probit method as the dose which is sufficient to prevent tonic seizure in half of the animals. The results are summarized in Table 4.

TABLE 4

| Test Compound | $ED_{50}$ (mg/kg) |
|---|---|
| Compound of Example 47 | 21 |
| Compound of Example 53 | 50–100 |
| Compound of Example 54 | 50–100 |
| Compound of Example 55 | 50 |

Toxicity

Compounds of Examples 5, 11, 14, 15 and 55 were orally or intraperitoneally administered to groups of five ddY-mice. All mice survived at the oral dose of 1000 mg/kg and at intraperitoneal dose of 300 mg/kg for five days after administration.

In view of the results of various pharmacological experiments including the above-mentioned experiments, the compounds of the present invention or pharmaceutically acceptable acid addition salts thereof are proved to exhibit inhibitory activity on gastric secretion, protective effect on gastric mucous membrane, anti-hypoxia activity, anti-amnesia activity and antianxiety activity. These compounds, therefore, are each useful as an active substance for use not only in the treatment of peptic ulcer, acute or chronic gastritis and acute damage of gastric mucous membrane but also in the treatment of dimentia and anxiety.

The compounds of the present invention can be safely administered orally or parenterally, i.e. intraperitoneally, intraveneously or subcutaneously, in human beings in the form of a pharmaceutical composition such as tablets, sugar-coated tablets, powder, granules, pills, syrup, injectable solutions or suppositories.

The pharmaceutical composition can be prepared by, for example, mixing a therapeutically effective amount of the compound of the present invention with a conventional and pharmaceutically acceptable additive such as an excipient, an extender or a diluent. The choice of such additive is determined by the preferred form of administration, the solubility of the compound and standard pharmaceutical practice.

The dose may vary depending upon the diseases to be treated or the conditions of the patients to be treated, but the daily dose for human adults preferably ranges from 3 to 300 mg in one to several divided doses.

| Formulation Example: 30.0 mg tablets can be prepared according to the following compositions | |
|---|---|
| Compound of Example 1 | 30.0 mg |
| Lactose | 50.0 mg |
| Corn Starch | 15.5 mg |
| Microcrystalline cellulose | 20.0 mg |
| Talc | 4.0 mg |
| Magnesium stearate | 0.5 mg |
| | 120.0 mg |

Compound of Example 1, lactose and corn starch are charged with a kneader and mixed well. A 5% corn starch binder is added and the mixture is granulated and dried. The granules are passed through a 24 mesh sieve and talc and magnesium stearate are added. The mixture is compressed with a punch having a diameter of 7 mm into tablets weighing 120 mg each.

PREPARATIVE EXAMPLES OF STARTING COMPOUNDS

Preparative Example 1

To a solution of 40 g of 2-acetylaminomethylthiophene and 30.3 g of acetylchloride in 600 ml of dichloroethane is added a small portion of 76.3 g of anhydrous aluminum chloride under cooling at 5°–10° C. After the mixture is stirred at 10° C. for 30 minutes and poured into ice-cold water, the precipitated crystals are collected by filtration to give 2-acetylaminomethyl-5-acetylthiophene, melting F- at 129°–130° C.

Preparative Example 2

To a solution of 40.3 g of 2-acetylaminomethyl-5-acetylthiophene in 500 ml of chloroform is added dropwise bromine under cooling with ice at 5°–10° C., and the mixture is stirred at room temperature for 30 minutes. After the resulting mixture is washed with water, dried over anhydrous magnesium sulfate and concentrated, the residue is recrystallized from ethanol to give 2-acetylaminomethyl-5-bromoacetylthiophene, melting at 129°–131° C.

Preparative Example 3

To a solution of 5.0 g of 2-acetylaminomethylthiophene and 4.4 g of chloroacetylchloride in 100 ml of dichloromethane is added a small portion of 8.6 g of anhydrous aluminum chloride at room temperature, and the mixture is refluxed with stirring for an hour and poured into ice-cold water. The precipitated crystals are collected by filtration to give 2-acetylaminomethyl-5-chloroacetylthiophene, melting at 146°–148° C.

Preparative Example 4

To a solution of 23 g of 2-(4-chlorobutyl)thiophene and 17.9 g of chloroacetyl chloride in 250 ml of dichloromethane is added a small portion of 21 g of aluminum chloride under cooling at 0°–5° C. and with stirring. After stirring under cooling with ice for 2 hours, the resultant mixture is poured into water and the organic layer is separated. The water layer is extracted with chloroform and the extract is combined with the organic layer. The combined organic layer is washed with water and dried over magnesium sulfate. The solvent is distilled off under reduced pressure to give 30 g of 2-chloroacetyl-5-(4-chlorobutyl)thiophene as a brown oil. To a solution of the oil in 300 ml of ethanol is added 11 g of thiourea, and refluxed on a water bath for 2 hours. After the solvent is concentrated under reduced pressure, water is added to the residue and the precipitated crystalline hydrochloride is collected by filtration.

To a suspension of the crystals in a mixture of water and ethyl acetate is added sodium hydrogencarbonate until the mixture is made alkaline. The organic layer is separated, washed with water and dried over magnesium sulfate. After the is distilled off under reduced pressure, the residue is recrystallized from ethanol to give 2-amino-4-[5-(4-chlorobutyl)-2-thienyl] thiazole as pale yellow crystals, melting at 99°–100° C.

The following compounds can be prepared in a similar manner:

2-Amino-4-[5-(2-chloroethyl)-2-thienyl]thiazole, melting at 153°–155° C.

2-Amino-4-[5-(3-chloropropyl)-2-thienyl]thiazole, melting at 117°–120° C.

The following examples will explain the present invention in more detail, but they are not to be construed as limiting the present invention.

EXAMPLE 1

A mixture of 37.3 g of 2-acetylamino-5-chloroacetyl-thiophene and 13.5 g of thiourea is refluxed with heating for 4 hours in ethanol, and cooled. The precipitated crystals (38.2 g) are collected by filtration and recrystallized from ethanol to give 2-amino-4-(5-acetylaminomethyl-2-thienyl)thiazole hydrochloride, melting at 216°–217° C. with decomposition.

The following compounds can be prepared in a similar manner as Example 1:

EXAMPLE 2

2-Guanidino-4-[5-(2-acetylaminoethyl)-2-thienyl]-thiazole, melting at 223°–224° C. with decomposition.

EXAMPLE 3

2-Guanidino-4-(5-acetylaminomethyl)-2-thienyl)-thiazole, melting at 210° C. with decomposition.

EXAMPLE 4

2-Amino-4-(5-diethylaminomethyl-2-thienyl)thiazole fumarate, melting at 203°–205° C. with decomposition.

EXAMPLE 5

2-Amino-4-(5-morpholinomethyl-2-thienyl)thiazole, melting at 181°–183° C. with decomposition.

EXAMPLE 6

2-Amino-4-(5-piperidinomethyl-2-thienyl)thiazole fumarate, melting at 235° C. with decomposition.

EXAMPLE 7

2-Amino-4-(5-isopropylaminomethyl-2-thienyl)-thiazole maleate, melting at 206°–207° C. with decomposition.

EXAMPLE 8

2-Amino-4-[5-(2-acetylaminoethyl)-2-thienyl]thiazole hydrochloride, melting at 220° C. with decomposition

EXAMPLE 9

To a suspension of 38.2 g of 2-amino-4-(5-acetylaminomethyl-2-thienyl)thiazole hydrochloride in 400 ml of water is added 56 g of concentrated sulfuric acid, and the mixture is stirred for 12 hours on a boiling water bath. The resulting mixture is cooled and the precipitated crystals are collected by filtration. A suspension of the crystals in 1 liter of water is made alkaline with potassium hydroxide and precipitated crystals are collected by filtration to give 28 g of crude crystals.

The crude crystals are recrystallized from methanol to give 2-amino-4-(5-aminomethyl-2-thienyl)thiazole, melting at 189° C. with decomposition.

The following compound can be prepared in a similar manner as Example 9:

EXAMPLE 10

2-Amino-4-[5-(2-aminoethyl)-2-thienyl]thiazole, melting at 160°–161° C. with decomposition.

EXAMPLE 11

To a suspension of 2-amino-4-(5-aminomethyl-2-thienyl) thiazole in 150 ml of chloroform is added 10 ml of triethylamine, and 3.1 g of acetoxyacetylchloride is added dropwise with stirring at room temperature (10°–35° C.). The whole mixture is stirred at room temperature for an hour, and then washed with water. The organic layer is separated, dried over anhydrous magnesium sulfate and concentrated under reduced pressure. The residue is recrystallized from ethanol to give 2-amino-4-(5-acetoxyacetylaminomethyl-2-thienyl) thiazole, melting at 149°–150° C. The corresponding maleate melts at 153°–154° C. with decomposition.

EXAMPLE 12

To a solution of 4.0 g of 2-amino-4-(5-aminomethyl-2-thienyl)thiazole in 100 ml of ethanol is added 2.85 g of ethyl nicotinate, and refluxed for 8 hours. After the reaction mixture is cooled with ice, the precipitated crystals are collected by filtration and recrystallized from dimethylformamide to give 2-amino-4-(5-nicotinoylaminomethyl-2-thienyl)thiazole, melting at 240°–241° C. with decomposition.

EXAMPLE 13

To a solution of 5.4 g of 3,4,5-trimethoxybenzoate in 100 ml of chloroform is added 4.0 g of 2-amino-4-(5-aminomethyl-2-thienyl)thiazole under cooling with ice at −5° C. to 0° C., and stirred at 15° C. to 25° C. for 4 hours. After the resulting mixture is cooled with ice, the precipitated crystals are collected by filtration and recrystallized from methanol to give 2-amino-4-[5-(3,4,5-trimethoxybenzoylaminomethyl)-2-thienyl]thiazole, melting at 217° C. with decomposition.

The following compounds can be prepared in a similar manner as Examples 12 and 13:

EXAMPLE 14

2-Amino-4-(5-ethoxyacetylaminomethyl-2-thienyl)-thiazole, melting at 130°–131° C.

EXAMPLE 15

2-Amino-4-(5-phenoxyacetylaminomethyl-2-thienyl)-thiazole maleate, melting at 148°–150° C. with decomposition.

EXAMPLE 16

2-Amino-4-[5-(4-methyl-1-piperazinylacetylaminomethyl)-2-thienyl]thiazole, melting at 149°–150° C.

EXAMPLE 17

2-Amino-4-[5-(2-acetoxyacetylaminoethyl)-2-thienyl]thiazole, melting at 112°–113° C. with decomposition.

EXAMPLE 18

2-Amino-4-[5-(2-(3,4,5-trimethoxybenzoylamino)ethyl)-2-thienyl]thiazole, melting at 174°–175° C.

EXAMPLE 19

2-Amino-4-[5-(2-nicotinoylaminoethyl)-2-thienyl]thiazole, melting at 190°–191° C. with decomposition.

EXAMPLE 20

2-Amino-4-[5-(2-(4-methyl-1-piperazinylacetylamino) ethyl)-2-thienyl]thiazole monohydrate, melting at 134°–138° C. with decomposition.

EXAMPLE 21

2-Amino-4-(5-hydroxyacetylaminomethyl)-2-thienyl) thiazole, melting at 175° C. with decomposition.

EXAMPLE 22

2-Amino-4-[5-(2-hydroxyacetylaminoethyl)-2-thienyl]thiazole, melting at 178°–179° C. with decomposition.

EXAMPLE 23

2-Guanidino-4-[5-(2-hydroxyacetylaminoethyl)-2-thienyl]thiazole, melting at 218°–219° C. with decomposition.

EXAMPLE 24

2-Amino-4-[5-(2-(3,3-dimethylureido)ethyl)-2-thienyl]thiazole, melting at 203°–204° C.

EXAMPLE 25

2-Amino-4-[5-(3-nitrophenoxyacetylaminomethyl)-2-thienyl]thiazole, melting at 182°–184° C.

EXAMPLE 26

2-Guanidino-4-(5-acetoxyacetylaminomethyl-2-thienyl]thiazole

EXAMPLE 27

2-Guanidino-4-(5-hydroxyacetylaminomethyl-2-thienyl) thiazole

EXAMPLE 28

2-Amino-4-[5-(3-dimethylaminomethylphenoxyacetylaminomethyl)-2-thienyl]thiazole

EXAMPLE 29

2-Amino-4-[5-(3-piperidinomethylphenoxyacetylaminomethyl)-2-thienyl]thiazole oxalate, melting at 105°–108° C. with decomposition.

EXAMPLE 30

2-Amino-4-[5-(3-chlorophenoxyacetylaminomethyl)-2-thienyl]thiazole, melting at 160°–162° C.

EXAMPLE 31

2-Amino-4-[5-(3-dimethylaminophenoxyacetylaminomethyl)-2-thienyl]thiazole

EXAMPLE 32

2-Amino-4-[5-(4-methoxyphenoxyacetylaminomethyl)-2-thienyl]thiazole

EXAMPLE 33

2-Amino-4-[5-(4-dimethylaminomethyl-2-pyridyloxyacetylaminomethyl)-2-thienyl]thiazole

EXAMPLE 34

2-Amino-4-[5-(3-dimethylaminomethylphenoxy)propionylaminomethyl)-2-thienyl]thiazole

EXAMPLE 35

2-Amino-4-[5-(3-acetoxypropionylaminomethyl)-2-thienyl]thiazole

EXAMPLE 36

2-Amino-4-[5-(4-dimethylaminobutoxyacetylaminomethyl)-2-thienyl]thiazole

EXAMPLE 37

2-Amino-4-[5-(3-(4-dimethylaminomethyl-2-pyridyloxy) propionylaminomethyl)-2-thienyl]thiazole

EXAMPLE 38

2-Amino-4-(5-isobutyryloxyacetylaminomethyl-2-thienyl) thiazole

EXAMPLE 39

To a solution of 2.0 g of 2-amino-4-(5-acetylaminomethyl-2-thienyl]thiazole in 50 ml of acetic acid is added dropwise a solution of 1.44 g of bromine in 10 ml of acetic acid with stirring at room temperature for 15 minutes. After the whole mixture is stirred for an hour, the precipitated crystals are collected by filtration and washed with ether to give 2-amino-4-(5-acetylaminomethyl-2-thienyl)-5-bromothiazole hydrobromide, melting at 185° C.–186° C. with decomposition.

EXAMPLE 40

To a solution of 5.0 g of 2-amino-4-(5-acetylaminomethyl-2-thienyl]thiazole in 50 ml of dimethylformamide are added 4.9 g of propyl bromide and 5.5 g of potassium carbonate, and stirred at 70° C. for 3 hours. The resultant mixture is poured into 200 ml of water and extracted with ethyl acetate. The extract is washed with water, dried and then concentrated under reduced pressure. After the residue is crystallized from ethanol, the crystals are collected by filtration and recrystallized from ethanol to give 2-dipropylamino-4-(5-acetylaminomethyl-2-thienyl)thiazole.

EXAMPLE 41

To a suspension of 5.0 g of 2-amino-4-(5-acetylaminomethyl-2-thienyl]thiazole in 200 ml of chloroform is added 12 ml of triethylamine, and is added dropwise 1.7 g of acetyl chloride with stirring at room temperature. The whole mixture is stirred at room temperature for an hour. After completion of the reaction, the resultant mixture is washed with water, dried over anhydrous magnesium sulfate, and concentrated under reduced pressure. After the residue is crystallized from ethanol, the crystals are collected by filtration and recrystallized from ethanol to give 2-acetylamino-4-(5-acetylaminomethyl-2-thienyl)thiazole, melting at 251° C. with decomposition.

EXAMPLE 42

A mixture of 5.43 g of 2-amino-4-[5-(4-chlorobutyl)-2-thienyl]thiazole, 4.0 g of 4-phenylpiperazine, 3.2 g of potassium carbonate, 0.1 g of potassium iodide and 50 ml of dimethylformamide is stirred at 70°–80° C. for 15 hours. The resultant mixture is poured into water and extracted with water. The extract is washed with water and dried over magnesium sulfate. After the solvent is distilled off under reduced pressure, the residue is recrystallized from ethanol to give 2-amino-4-[5-(4-(4-phenyl-1-piperazinyl) butyl)-2-thienyl]thiazole, melting at 165°–167° C.

The following compounds can be prepared in a similar manner as any of the above Examples:

EXAMPLE 43
2-Amino-4-(5-phenylthioacetylaminomethyl-2-thienyl) thiazole, melting at 144°–146° C. with decomposition.

EXAMPLE 44
2-Amino-4-(5-benzyloxyacetylaminomethyl-2-thienyl) thiazole, melting at 140°–144° C.

EXAMPLE 45
2-Amino-4-[5-(4-fluorophenoxyacetylaminomethyl)-2-thienyl]thiazole, melting at 145°–148° C.

EXAMPLE 46
2-Amino-4-[5-(2-bromophenoxyacetylaminomethyl)-2-thienyl]thiazole, melting at 167°–169° C.

EXAMPLE 47
2-Amino-4-[5-(2-(4-(3-trifluoromethylphenyl)-1-piperazinyl)ethyl)-2-thienyl]thiazole, melting at 135°–140° C.

EXAMPLE 48
2-Guanidino-4-(5-phenoxyacetylaminomethyl-2-thienyl) thiazole maleate, melting at 177°–178° C.

EXAMPLE 49
2-Amino-4-[5-(3-acetylthiopropionylaminomethyl)-2-thienyl]thiazole maleate, melting at 168°–169° C. with decomposition.

EXAMPLE 50
2-Amino-4-[5-(2-phenoxypropionylaminomethyl)-2-thienyl]thiazole maleate, melting at 154°–157° C. with decomposition.

EXAMPLE 51
2-Guanidino-4-(5-piperidinomethyl-2-thienyl)-thiazole, melting at 226°–228° C. with decomposition.

EXAMPLE 52
2-Amino-4-(5-acetylamino-3-thienyl)thiazole, melting at 229° C. with decomposition.

EXAMPLE 53
2-Phenylamino-4-(5-piperidinomethyl-2-thienyl)-thiazole, melting at 120°–121° C.

EXAMPLE 54
2-Amino-4-[5-(2-piperidinoethyl)-2-thienyl]thiazole maleate, melting at 130° C. with decomposition.

EXAMPLE 55
2-Amino-4-[5-(2-(4-(3-chlorophenyl)-1-piperazinyl)ethyl)-2-thienyl]thiazole hydrochloride, melting at 236° C. with decomposition.

EXAMPLE 56
2-Amino-4-[5-(3-aminophenoxyacetylaminomethyl)-2-thienyl]thiazole, melting at 164°–166° C.

EXAMPLE 57
2-Amino-4-(5-pivaloyloxyacetylaminomethyl-2-thienyl) thiazole, melting at 172°–174° C.

EXAMPLE 58
2-Amino-4-(5-butyryloxyacetylaminomethyl-2-thienyl) thiazole maleate, melting at 145°–147° C. with decomposition.

EXAMPLE 59
2-Amino-4-(5-benzoyloxyacetylaminomethyl-2-thienyl) thiazole, melting at 180°–181° C.

EXAMPLE 60
2-Amino-4-(5-hexanoyloxyacetylaminomethyl-2-thienyl) thiazole maleate, melting at 143°–145° C. with decomposition.

EXAMPLE 61
2-Amino-4-[5-(3,3-dimethylureidomethyl)-2-thienyl]-thiazole, melting at 155°–157° C.

EXAMPLE 62
2-Amino-4-(5-acetylthioacetylaminomethyl-2-thienyl) thiazole, melting at 149°–150° C.

EXAMPLE 63
2-Amino-4-[5-(2-(4-(4-fluorophenyl)-1-piperazinyl) ethyl)-2-thienyl]thiazole, melting at 195°–200° C. with decomposition.

EXAMPLE 64
2-Amino-4-[5-(2-(4-phenyl-1-piperazinyl)ethyl)-2-thienyl]thiazole, melting at 115°–120° C. with decomposition.

EXAMPLE 65
2Amino-4-[5-(2-morpholinoethyl)-2-thienyl]thiazole, melting at 180°–182° C. with decomposition.

EXAMPLE 66
2-Amino-4-[5-(4-(4-(3-trifluoromethylphenyl)-1-piperazinyl)butyl)-2-thienyl]thiazole, melting at 149°–150° C.

EXAMPLE 67
2-Allylamino-4-(5-morpholinomethyl-2-thienyl]-thiazole maleate, melting at 142°–143° C.

EXAMPLE 68
2-Amino-4-[5-(4-(4-(2-pyrimidinyl)-1-piperazinyl)-butyl)-2-thienyl]thiazole, melting at 147.5°–148.5° C.

EXAMPLE 69
2-Benzoylamino-4-(5-piperidinomethyl-2-thienyl)-thiazole, melting at 164°–166° C.

EXAMPLE 70
2-Amino-4-[5-(3-(4-(3-trifluoromethylphenyl)-1-piperazinyl)propyl)-2-thienyl]thiazole, melting at 113°–115° C.

EXAMPLE 71

2-Amino-4-[5-(3-morpholinopropyl)-2-thienyl]-thiazole, melting at 148°–150° C.

EXAMPLE 72

2-Amino-4-[5-(4-(4-(3-chlorophenyl)-1-piperazinyl) butyl)-2-thienyl]thiazole, melting at 171°–172° C.

EXAMPLE 73

2-Amino-4-[5-(4-morpholinobutyl)-2-thienyl]-thiazole, melting at 177°–178° C.

EXAMPLE 74

2-Amino-4-[5-(3-(1-pyrrolidinyl)propyl)-2-thienyl]-thiazole, melting at 107°–110° C.

EXAMPLE 75

2-Butylamino-4-(5-morpholinomethyl-2-thienyl]-thiazole fumarate, melting at 163°–164° C.

EXAMPLE 76

2-Benzoylamino-4-(5-morpholinomethyl-2-thienyl) thiazole fumalate, melting at 221°–223° C.

EXAMPLE 77

2-Amino-4-[5-(3-(4-methyl-1-piperazinyl)propyl)-2-thienyl]thiazole, melting at 167°–168° C.

EXAMPLE 78

2-Dipropylamino-4-(5-morpholinomethyl-2-thienyl) thiazole,
$^1$H-NMR (CDCl$_3$) ppm: 0.8–1.1 (6H, t); 1.4–1.9 (4H, m); 2.2–2.6, 3.5–3.8 (8H, m); 3.2–3.5 (4H, t); 3.9 (2H, s); 6.4 (1H, s); 6.8 (1H, d); 7.2 (1H, d).

EXAMPLE 79

2-Amino-4-(4-aminomethyl-2-thienyl)thiazole

EXAMPLE 80

2-Amino-4-(4-acetylaminomethyl-2-thienyl)thiazole

EXAMPLE 81

2-Amino-4-(4-acetoxyacetylaminomethyl-2-thienyl)-thiazole

EXAMPLE 82

2-Amino-4-(4-phenoxyacetylaminomethyl-2-thienyl) thiazole

EXAMPLE 83

2-Amino-4-[4-(3-dimethylaminomethylphenoxyacetylaminomethyl)-2-thienyl]thiazole

EXAMPLE 84

2-Amino-4-[4-(3-piperidinomethylphenoxyacetylaminomethyl)-2-thienyl]thiazole

EXAMPLE 85

2-Amino-4-[4-(4-dimethylaminomethyl-2-pyridyloxyacetylaminomethyl)-2-thienyl]thiazole

EXAMPLE 86

2-Amino-4-(4-ethoxyacetylaminomethyl)-2-thienyl)-thiazole

EXAMPLE 87

2-Amino-4-(4-diethylaminomethyl-2-thienyl)thiazole

EXAMPLE 88

2-Amino-4-(4-isopropylaminomethyl-2-thienyl)-thiazole

EXAMPLE 89

2-Amino-4-(4-piperidinomethyl-2-thienyl)thiazole

EXAMPLE 90

2-Guanidino-4-(4-acetoxyacetylaminomethyl-2-thienyl) thiazole

EXAMPLE 91

2-Guanidino-4-[4-(2-acetoxyacetylaminoethyl)-2-thienyl]thiazole

EXAMPLE 92

2-Amino-4-[4-(3-acetoxypropionylaminomethyl)-2-thienyl]thiazole

EXAMPLE 93

2-Amino-4-[4-(3-phenoxypropionylaminomethyl)-2-thienyl]thiazole

EXAMPLE 94

2-Amino-4-[4-(3-ethoxypropionylaminomethyl)-2-thienyl]thiazole

EXAMPLE 95

2-Amino-4-[4-(3-(3-dimethylaminomethylphenoxy) propionylaminomethyl)-2-thienyl]thiazole

EXAMPLE 96

2-Amino-4-[4-(3-(3-piperidinomethylphenoxy)propionylaminomethyl)-2-thienyl]thiazole

EXAMPLE 97

2-Amino-4-[4-(3-(4-dimethylaminomethyl-2-pyridyloxy) propionylaminomethyl)-2-thienyl]thiazole

EXAMPLE 98

2-Amino-4-(5-aminomethyl-3-thienyl)thiazole

EXAMPLE 99

2-Amino-4-(5-acetylaminomethyl-3-thienyl)thiazole

EXAMPLE 100

2-Amino-4-(5-acetoxyacetylaminomethyl-3-thienyl)-thiazole

EXAMPLE 101

2-Amino-4-(5-phenoxyacetylaminomethyl-3-thienyl)-thiazole

EXAMPLE 102

2-Amino-4-[5-(3-piperidinomethylphenoxyacetylaminomethyl)-3-thienyl]thiazole

EXAMPLE 103

2-Amino-4-[5-(3-dimethylaminomethylphenoxyacetylaminomethyl)-3-thienyl]thiazole

EXAMPLE 104

2-Amino-4-[5-(4-dimethylaminomethyl-2-pyridyloxyacetylaminomethyl)-3-thienyl]thiazole

EXAMPLE 105

2-Amino-4-(5-ethoxyacetylaminomethyl-3-thienyl)-thiazole

EXAMPLE 106

2-Amino-4-(5-isopropylaminomethyl-3-thienyl)-thiazole

EXAMPLE 107

2-Amino-4-(5-dimethylaminomethyl-3-thienyl)-thiazole

EXAMPLE 108

2-Amino-4-(5-piperidinomethyl-3-thienyl)thiazole

EXAMPLE 109

2-Amino-4-(5-acetylamino-2-thienyl)thiazole

EXAMPLE 110

2-Isopropylamino-4-(5-acetylaminomethyl-2-thienyl)thiazole

EXAMPLE 111

2-Diethylamino-4-(5-acetylaminomethyl-2-thienyl)-thiazole

EXAMPLE 112

2-Isopropylamino-4-(5-aminomethyl-2-thienyl)-thiazole

EXAMPLE 113

2-Diethylamino-4-(5-aminomethyl-2-thienyl)thiazole

EXAMPLE 114

2-Acetylamino-4-(5-aminomethyl-2-thienyl)thiazole

EXAMPLE 115

2-Guanidino-4-(5-aminomethyl-2-thienyl)thiazole

EXAMPLE 116

2-Guanidino-4-[5-(2-aminoethyl)-2-thienyl]thiazole

EXAMPLE 117

2-Isopropylamino-4-(5-acetocyacetylaminomethyl-2-thienyl)thiazole

EXAMPLE 118

2-Diethylamino-4-(5-acetoxyacetylaminomethyl-2-thienyl)thiazole

EXAMPLE 119

2-Acetylamino-4-(5-acetoxyacetylaminomethyl-2-thienyl)thiazole

EXAMPLE 120

2-Amino-4-[5-(3-acetoxyacetylaminopropyl)-2-thienyl]thiazole

EXAMPLE 121

2-Amino-4-[5-(4-acetoxyacetylaminobutyl)-2-thienyl]thiazole

Although the present invention has been adequately discussed in the foregoing specification and examples included therein, one readily recognizes that various changes and modifications may be made without departing from the spirit and scope thereof.

What is claimed is:

1. A thienylthiazole compound of the formula:

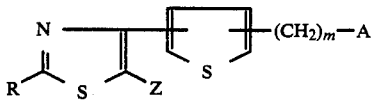

or a pharmaceutically acceptable acid addition salt thereof, wherein

R is (1) amino, (2) guanidino, (3) mono- or di-$C_{1-6}$ alkylamino, (4) $C_{2-5}$ alkenylamino, (5) mono- or di-phenylamino which is unsubstituted or substituted on the phenyl nucleus by at least one substituent selected from the group consisting of halogen, $C_{1-4}$ alkyl, trifluoromethyl, $C_{1-4}$ alkoxy, nitro and amino, (6) $C_{2-5}$ alkanoylamino or (7) benzoylamino which is unsubstituted or substituted on the phenyl nucleus by at least one substituent selected from the group consisting of halogen, $C_{1-4}$ alkyl, trifluoromethyl, $C_{1-4}$ alkoxy, nitro and amino;

A is (1) amino, (2) mono- or di-$C_{1-6}$ alkylamino, (3) a saturated 5 to 7 membered cyclic ring amino which may further contain at least one heteroatom selected from the group consisting of oxygen and optionally substituted nitrogen, (4) $C_{2-5}$ alkanoylamino, (5) a group of the formula

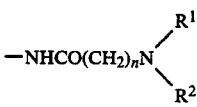

in which each of $R^1$ and $R^2$ is hydrogen or $C_{1-10}$ alkyl, or $R^1$ and $R^2$ together with the adjacent nitrogen atom form a saturated or unsaturated 5 to 7 membered heterocycle which may further contain at least one heteroatom selected from the group consisting of oxygen and optionally substituted nitrogen, and n is 0 or an integer of 1 to 3, (6) a group of the formula:

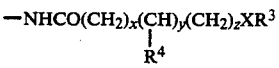

in which $R^3$ is (a) hydrogen, (b) $C_{1-10}$ alkyl, (c) $C_{2-12}$ alkanoyl, (d) mono- or di-$C_{1-5}$ alkylamino-$C_{1-4}$ alkyl, or (e) phenyl, naphthyl, benzyl, 2-phenylethyl, 3-phenylpropyl, pyridyl, furyl or thienyl which is unsubstituted or ring-substituted by at least one substituent selected from the group consisting of halogen, amino, nitro, $C_{1-4}$ alkyl, $C_{1-4}$ alkoxy, mono- or di-$C_{1-6}$ alkylamino, mono- or di-$C_{1-5}$ alkylamino-$C_{1-4}$ alkyl and a saturated 5 to 7 membered cyclic amino-$C_{1-4}$ alkyl which may further contain, in the cyclic amino moiety, at least one heteroatom selected from the group consisting of oxygen and optionally substituted nitrogen, $R^4$ is hydrogen or $C_{1-10}$ alkyl, X is oxygen or sulfur, and each of x, y and z is 0 or an integer of 1 to 3 provided that the sum of x, y and z is 3 or less, or (7) a group of the formula:

in which $R^5$ is phenyl, naphthyl, benzyl, 2-phenylethyl, 3-phenylpropyl, pyridyl, furyl or thienyl which is unsubstituted or ring-substituted by at least one substituent selected from the group consisting of halogen, amino, nitro, $C_{1-4}$ alkyl, $C_{1-4}$ alkoxy, mono- or di-$C_{1-6}$ alkylamino, mono- or di-$C_{1-5}$ alkylamino-$C_{1-4}$ alkyl and a saturated 5 to 7 membered cyclic amino-$C_{1-4}$ alkyl which may further contain, in the cyclic amino moiety, at least one heteroatom selected from the group consisting of oxygen and optionally substituted nitrogen;

Z is hydrogen or halogen; and m is 0 or an integer of 1 to 4.

2. The thienylthiazole compound of claim 1, wherein R is amino or phenylamino; A is amino, mono- or di-$C_{1-6}$ alkylamino, a saturated 5 to 7 membered cyclic ring amino which may further contain at least one heteroatom selected from the group consisting of oxygen and optionally substituted nitrogen, $C_{2-5}$ alkanoylamino or the group of the formula:

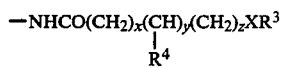

wherein each symbol is as defined in claim 5; Z is hydrogen; and m is 0 or an integer of 1 to 4.

3. The thienylthiazole compound of claim 1 selected from the group consisting of 2-amino-4-(5-acetoxyacetylaminomethyl-2-thienyl)thiazole, 2-amino-4-(5-acetylaminomethyl-2-thienyl)thiazole, 2-amino-4-(5-diethylaminomethyl-2-thienyl)thiazole, 2-amino-4-(5-morpholinomethyl-2-thienyl) thiazole, 2-amino-4-(5-piperidinomethyl-2-thienyl)thiazole, 2-amino-4-(5-isopropylaminomethyl-2-thienyl)thiazole, 2-amino-4-(5-ethoxyacetylaminomethyl-2-thienyl)thiazole, 2-amino-4-(5-phenoxyacetylaminomethyl-2-thienyl)thiazole, 2-amino-4-[5-(2-(4-(3-trifluoromethylphenyl)-1-piperazinyl) ethyl)-2-thienyl]thiazole, 2-amino-4-[5-(2-phenoxypropionylaminomethyl-2-thienyl]thiazole, 2-phenylamino-4-(5-piperidinomethyl-2-thienyl)thiazole, 2-amino-4-[5-(2-piperidinoethyl)-2-thienyl]thiazole, 2-amino-4-[5-(2-(4-(3-chlorophenyl)-1-piperazinyl)ethyl)2-thienyl]thiazole, 2-amino-4-[5-(2-morpholinoethyl)-2-thienyl]thiazole and pharmaceutically acceptable acid addition salts thereof.

4. A pharmaceutical composition for treatment of peptic ulcer, acute or chronic gastritis, acute damage of gastric mucous membrane, dimentia or anxiety, comprising a therapeutically effective amount of the compound of claim 1 with a pharmaceutically acceptable additive.

* * * * *